United States Patent
Deeg

(10) Patent No.: US 7,380,466 B2
(45) Date of Patent: Jun. 3, 2008

(54) APPARATUS AND METHOD FOR DETERMINING MECHANICAL PROPERTIES OF CEMENT FOR A WELL BORE

(75) Inventor: Wolfgang F. J. Deeg, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 463 days.

(21) Appl. No.: 11/206,719

(22) Filed: Aug. 18, 2005

(65) Prior Publication Data

US 2007/0056383 A1    Mar. 15, 2007

(51) Int. Cl.
G01N 3/00    (2006.01)
G01N 17/00    (2006.01)

(52) U.S. Cl. ........................................ 73/803; 73/865.6

(58) Field of Classification Search ............... 73/856.5, 73/866, 803, 865.6
See application file for complete search history.

(56) References Cited

U.S. PATENT DOCUMENTS

| | | | |
|---|---|---|---|
| 3,574,281 A | 4/1971 | Casey et al. | |
| 3,619,463 A | 11/1971 | Budin et al. | |
| 3,779,085 A | 12/1973 | Rice | |
| 4,259,868 A | 4/1981 | Rao et al. | |
| 4,377,087 A | 3/1983 | Rodot | |
| 4,389,896 A * | 6/1983 | Babcock | 73/784 |
| 4,408,489 A | 10/1983 | Spangle | |
| 4,430,889 A | 2/1984 | Sutton | |
| 4,491,017 A | 1/1985 | Iyer | |
| 4,567,759 A | 2/1986 | Ekstrom et al. | |
| 4,567,765 A | 2/1986 | Rao et al. | |
| 4,607,530 A | 8/1986 | Chow | |
| 4,685,092 A | 8/1987 | Dumont | |
| 4,691,558 A | 9/1987 | Vinson et al. | |
| 4,703,427 A | 10/1987 | Catala et al. | |

(Continued)

FOREIGN PATENT DOCUMENTS

EP    0 124 383 A1    11/1984

(Continued)

OTHER PUBLICATIONS

Foreign communication related to a counterpart application dated Dec. 21, 2006.

(Continued)

Primary Examiner—Hezron E. Williams
Assistant Examiner—John Fitzgerald
(74) Attorney, Agent, or Firm—John W. Wustenberg; Fish & Richardson P.C.

(57) ABSTRACT

Apparatus for testing mechanical properties of a sample cement composition. The apparatus includes an annular test chamber and a variable stress system. The variable stress system communicates with the annular test chamber. The variable stress system is operable to control at least one of temperature or pressure applied to the sample cement composition in the annular test chamber during and after curing of the sample cement composition. One or more sensors are coupled to the annular test chamber. The sensors are operable to sense at least one of stress, strain and displacement from the sample cement composition in response to one or more changes applied to the annular test chamber by the variable stress system for determination of at least one mechanical property of the sample cement composition.

20 Claims, 4 Drawing Sheets

U.S. PATENT DOCUMENTS

| | | |
|---|---|---|
| 4,757,479 A | 7/1988 | Masson et al. |
| 4,809,237 A | 2/1989 | Vogel et al. |
| 4,823,594 A | 4/1989 | Gray |
| 4,848,145 A | 7/1989 | Blaschke et al. |
| 4,893,285 A | 1/1990 | Masson et al. |
| 4,896,303 A | 1/1990 | Leslie et al. |
| 4,970,695 A | 11/1990 | Huau |
| 5,009,512 A | 4/1991 | Lessi et al. |
| 5,089,989 A | 2/1992 | Schmidt et al. |
| 5,127,473 A | 7/1992 | Harris et al. |
| 5,216,638 A | 6/1993 | Wright |
| 5,233,863 A | 8/1993 | Surjaatmadja et al. |
| 5,325,723 A | 7/1994 | Meadows et al. |
| 5,353,637 A | 10/1994 | Plumb et al. |
| 5,377,160 A | 12/1994 | Tello et al. |
| 5,377,753 A | 1/1995 | Haberman et al. |
| 5,412,990 A | 5/1995 | D'Angelo et al. |
| 5,487,307 A | 1/1996 | Landgren et al. |
| 5,571,951 A | 11/1996 | Jamth |
| 5,741,971 A | 4/1998 | Lacy |
| 5,763,773 A | 6/1998 | Birchak et al. |
| 5,869,750 A | 2/1999 | Onan et al. |
| 5,969,059 A | 10/1999 | Murai et al. |
| 5,992,223 A | 11/1999 | Sabins et al. |
| 6,053,245 A | 4/2000 | Haberman |
| 6,055,874 A * | 5/2000 | Onan et al. ............... 73/865.6 |
| 6,070,662 A | 6/2000 | Ciglenec et al. |
| 6,112,599 A | 9/2000 | Maki, Jr. |
| H1932 H | 1/2001 | Heathman et al. |
| 6,227,039 B1 | 5/2001 | Te'eni |
| 6,269,684 B1 | 8/2001 | Maki, Jr. et al. |
| 6,345,535 B1 | 2/2002 | Sabins et al. |
| 6,484,568 B1 | 11/2002 | Griffith et al. |
| 6,527,438 B2 | 3/2003 | Zollinger et al. |
| 6,595,068 B2 * | 7/2003 | Brovold et al. ............... 73/803 |
| 6,644,402 B1 | 11/2003 | Sharma et al. |
| 6,655,213 B1 | 12/2003 | Reinhardt et al. |
| 6,782,735 B2 | 8/2004 | Walters et al. |
| 6,789,621 B2 | 9/2004 | Wetzel et al. |
| 6,817,238 B2 | 11/2004 | Boncan et al. |
| 6,829,922 B2 | 12/2004 | Patin et al. |
| 6,834,233 B2 | 12/2004 | Economides et al. |
| 6,874,353 B2 | 4/2005 | Johnson et al. |
| 6,918,292 B2 | 7/2005 | Go Boncan et al. |
| 7,089,816 B2 * | 8/2006 | Hakimuddin ................ 73/866 |
| 7,191,663 B2 * | 3/2007 | Go Boncan et al. .......... 73/803 |
| 7,240,545 B1 * | 7/2007 | Jennings .................... 73/149 |
| 2001/0037687 A1 * | 11/2001 | Brovold et al. ............... 73/826 |
| 2003/0150263 A1 | 8/2003 | Economides et al. |
| 2003/0221829 A1 | 12/2003 | Patel et al. |
| 2005/0126300 A1 | 6/2005 | Boncan et al. |
| 2005/0152432 A1 | 7/2005 | Hakimuddin |
| 2006/0225523 A1 * | 10/2006 | Reddy et al. ............... 73/865.6 |

FOREIGN PATENT DOCUMENTS

| | | |
|---|---|---|
| EP | 0 176 400 B1 | 4/1986 |
| EP | 0 176 408 B1 | 4/1986 |
| EP | 0 101 580 B1 | 12/1986 |
| EP | 0 110 750 B1 | 9/1988 |
| EP | 0 098 778 B1 | 3/1989 |
| EP | 0 198 985 B1 | 12/1989 |
| EP | 0 443 936 A1 | 8/1991 |
| EP | 0 395 499 B1 | 7/1993 |
| EP | 0 865 612 B1 | 6/2002 |
| EP | 1 541 987 A2 | 6/2005 |
| GB | 2 353 546 A | 2/2001 |
| GB | 2 354 026 A | 3/2001 |
| GB | 2 355 742 A | 5/2001 |
| GB | 2 386 625 A | 9/2003 |
| WO | WO 00/49273 | 8/2000 |
| WO | WO 2004/088302 A1 | 10/2004 |

OTHER PUBLICATIONS

Minear, J.W. et al. "Cement Sheath Evaluation", pp. 271-296, Petroleum Well Construction.

Love, A.E.H. "A Treatise on the Mechanical Theory of Elasticity".

Thiercelin, M.J. et al. "Cement Design Based On Cement Mechanical Response" SPE 52890, dated 1998.

Goodwin, K.J. et al. "Cement Sheath Stress Failure" SPE 20453, dated 1992.

Deeg, Wolfgang et al. "How Foamed Cement Advantages Extend to Hydraulic Fracturing Operations", World Oil, Nov. 1999.

"FlexiForce® Standard & Custom OEM Sensing Solutions" dated 2005.

* cited by examiner

APPARATUS AND METHOD FOR DETERMINING MECHANICAL PROPERTIES OF CEMENT FOR A WELL BORE

TECHNICAL FIELD

Slurry design for subterranean cementing operation, and more particularly, an apparatus and method for determining mechanical properties of cement for a well bore.

BACKGROUND

Oil and gas wells extend from the surface to one or more subterranean formations of rock containing oil and/or gas. The well is typically cased by cementing a steel or other suitable casing in the well bore. The casing stabilizes the sides of the well bore, prevents pollution of fresh water reservoirs and/or prevents fluids from zones other than oil and gas producing zones from entering the well bore.

Cementing operations pump wet cement slurry down a well bore to fill the space between the casing and the rock walls. The cement protects the casing and prevents water and other fluids from flowing vertically in the space between the casing and rock walls of the well bore. Typically, cementing operations are designed and supervised by engineers. Laboratory technicians test and select the cement slurry and additives.

Cement compositions are designed for a variety of well bore conditions, which may vary in depth, temperature and pressure. In designing a cement composition for a well bore, a number of potential slurries are typically tested for mechanical properties. Mechanical properties are often determined using circular cylinder samples. The samples are cured at pressure and temperature, depressurized, machined to proper geometry and dimensional tolerances, placed in a pressure vessel, re-loaded hydrostatically to a predetermined confining pressure, and then tested to failure. Another method for establishing mechanical properties is to measure acoustic velocities and calculate mechanical properties based on linear elastic theory and various empirical correlations. These dynamic measurements are performed at extremely high loading rates and the data is corrected for lower loading rates expected under in situ conditions.

SUMMARY

Apparatus and method are provided for determining mechanical properties of cement for a well bore. In accordance with one embodiment, an apparatus for testing mechanical properties of a sample cement composition includes an annular test chamber, a variable stress system and one or more sensors. The variable stress system communicates with the annular test chamber. The variable stress system is operable to control at least one of temperature or pressure applied to a sample cement composition in the annular test chamber during and after curing of the sample cement composition. The one or more sensors are coupled to the annular chamber and operable to sense at least one of stress, strain or displacement from the sample cement composition in response to one or more changes applied to the annular test chamber by the variable stress system for determination of at least one mechanical property of the sample cement composition.

In accordance with one or more specific embodiments, the variable stress system may comprise a variable pressure system operable to vary a pressure applied to the sample cement composition in the annular test chamber. In another embodiment, the variable pressure system may comprise a variable temperature system operable to vary the temperature applied to the sample cement composition in the annular test chamber. In these and other embodiments, the test cell may apply curing pressure and/or temperature to the sample cement composition during curing of the sample cement composition and/or incremental pressure changes to the sample cement composition after curing.

Technical advantages of one, some, all or none of the embodiments may include providing a test apparatus and method able to determine mechanical properties of cement at in-situ conditions without having to depressurize the sample after curing and prior to testing. A wide variety of sample cement compositions including, for example, foam and gas evolving cements, may be prepared and tested. Yield, associated plastic deformation and cracking from unloading and reloading a sample may be avoided. A determination of mechanical properties may be done without laboratory correlations between static and dynamic measurements.

The details of one or more embodiments of the laboratory apparatus and method for determining mechanical properties of cement for a well bore are set forth in the accompanying drawings and the description below. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Figure 1:
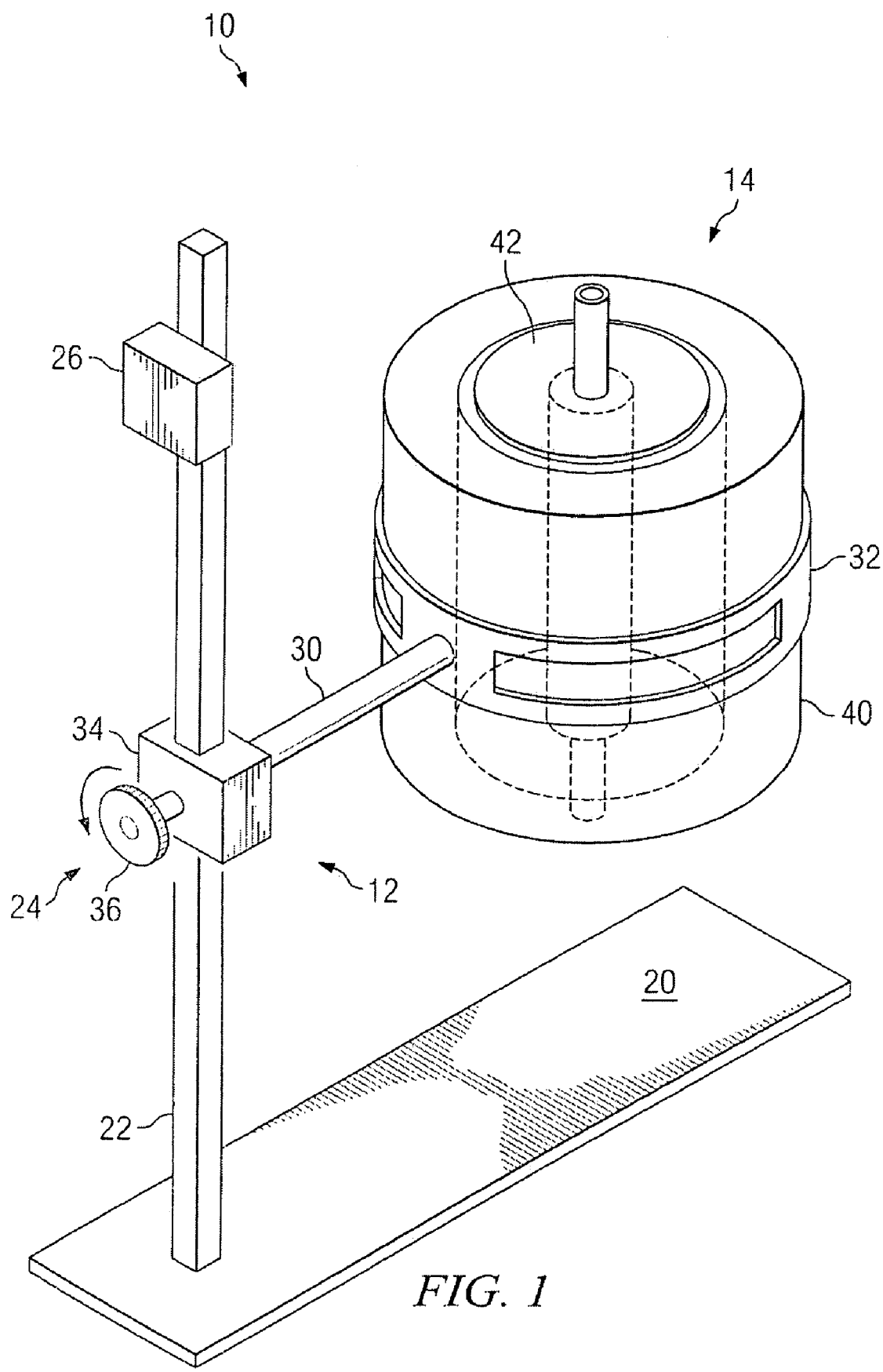
FIG. 1 is a schematic diagram illustrating one embodiment of a laboratory apparatus for evaluating cement for a well bore.

FIG. 1 illustrates one embodiment of a laboratory apparatus 10 for determining mechanical properties of cement for a well bore. As used herein, cement is a liquid mixture that hardens into solid and may be any sealant to bond casing or other piping to well walls or other well piping. The laboratory apparatus 10 may perform laboratory screening or other tests for a number of sample cement compositions to determine mechanical properties of the sample cement compositions at and/or for well bore conditions. Well bore conditions include pressure, temperature and/or other conditions simulating, matching, based on, designed for or otherwise corresponding to those in or expected in the well bore. The screening tests may allow a relatively large number of sample cement compositions to be tested for Young's modulus, Poisson's ratio, tensile strength and/or other mechanical properties. For example, screening tests may be performed on one, 10, 15, 20, 30 or more sample cement compositions in an initial stage of slurry design for the well bore. The laboratory apparatus 10 may be any suitable device in which sample cement compositions may be tested in scaled-down form under controlled or other variable stress conditions.

Referring to FIG. 1, the laboratory apparatus 10, in one embodiment, comprises a stand 12 and a test assembly 14. The stand 12 may include a base 20, spine 22, rotating arm 24 and a controller 26. The rotating arm 24 may comprise an arm 30 coupled to a clamp 32. The base 20, spine 22, and rotating arm 24 may comprise steel or other suitable materials for supporting the test assembly 14.

The clamp 32 secures the test assembly 14 to the arm 30. A bearing block 34 allows rotation of the arm 30 through the spine 22. A handle 36 may be provided at the end of the arm 30 to facilitate rotation of the test assembly 14. The handle 36 and/or bearing block 34 may include a lock for securing the test assembly 14 at various angles. For example, the test assembly 14 may be secured with its top up, down, or at other intermediate angles.

Controller 26 includes a centralized processing unit (CPU) or other suitable electronics for controlling and monitoring test performed in the test assembly 14. In one embodiment, the controller 26 may control pressure changes, temperature changes or other variable stress conditions applied to a sample cement composition in the test assembly 14. The variable stress conditions may be any variable force or condition applied to a sample cement composition in cured and/or uncured form that test performance over time. The variable stress conditions may be cyclic in that they recur in or are marked by cycles. The controller 26 may communicate with the one or more variable stress systems that apply the variable stress conditions and/or other test equipment over wireline, wireless or other suitable links.

The controller 26 may also include input/output devices, such as test controls and read-outs, as well as a database or other memory for reading, displaying and/or recording test conditions and test data. In one embodiment, the test data may include data from one or more sensors for measuring stress, strain, displacement or other mechanical forces in the test assembly 14. For example, the sensors may comprise contact force or contact stress sensors as well as strain gauges, fluid filled bladders, standard or other extensometers, and/or any suitable combination of these.

The test assembly 14 may comprise a pressure cell 40 and a test cell 42. The pressure cell 40 may raise, lower, cycle or otherwise vary pressures applied to an exterior and/or other part of the test cell 42. The pressure cell 40 may comprise an autoclave with electrical and/or other passthroughs and/or other pressure device. The pressure cell 40 may include an internal heating and/or cooling element or may comprise heating and cooling coils which may be connected to a temperature bath for temperature control.

The test cell 42 receives and holds a sample cement composition for testing. The test cell 42, as described in more detail below in connection with FIG. 2, includes ports for measuring cement shrinkage, sheath failure, other permeability changes and/or other performance criteria in response to pressure changes, temperature changes, or other stress variations. In one embodiment, the test cell 42 is completely reusable. In another embodiment, at least a portion of test cell 42 is reusable. In yet another embodiment, the test cell 42 may be entirely or partially disposable.

Figure 2:
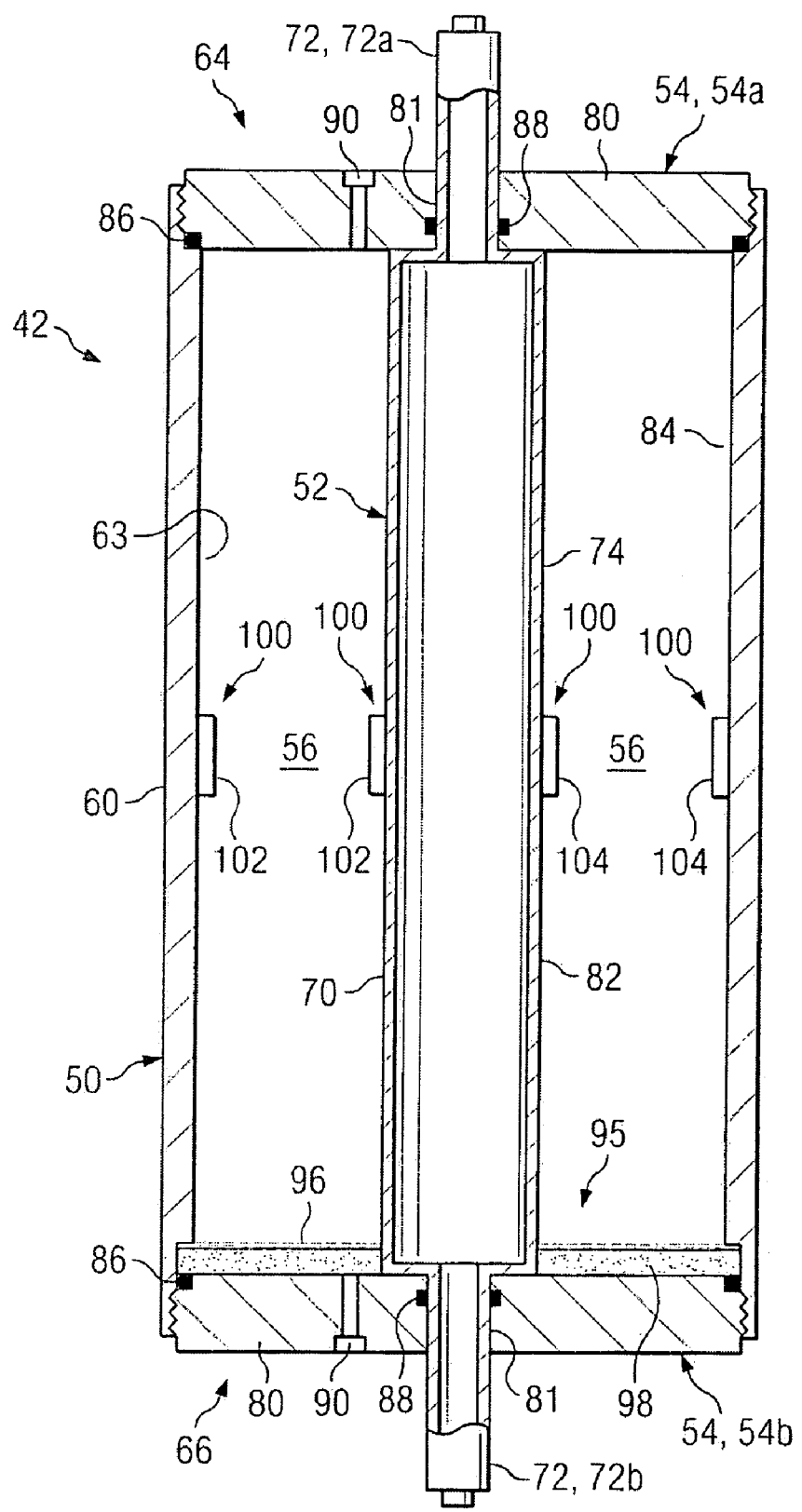
FIG. 2 is a cross-sectional diagram illustrating one embodiment of the test cell for the laboratory apparatus of FIG. 1.

FIG. 2 illustrates one embodiment of the test cell 42. The test cell 42 may be any device or other apparatus with a test chamber, connections and sensors for evaluation of mechanical properties of a sample cement composition under variable stress conditions such as, for example, variable or other controlled temperature and/or pressure conditions. In the illustrated embodiment, the test cell 42 comprises a pipe-in-pipe configuration and is reusable. The test cell 42 may be otherwise suitably configured and may be used for one, several or many screening tests. For example, the test cell 42 may comprise concentric PVC pipes with an inner pipe extending through end caps of the outer pipe and an o-ring or other suitable seal between the inner pipe and end cap of the outer pipe. One or more of the pipes may also comprise, for example, anodized aluminum, stainless steel, brass, and/or copper having a thickness of 3-5 millimeters.

Referring to FIG. 2, the test cell 42 includes an outer pipe 50, an inner pipe 52, and end caps 54. End caps 54 may comprise a top end cap 54a and a bottom end cap 54b. The outer pipe 50, inner pipe 52 and end caps 54 together form a test chamber 56 for receiving, holding and testing sample cement compositions. The outer pipe 50 and inner pipe 52 and end caps 54 may be inert to cement and may have mechanical properties chosen to improve or maximize parameters to be measured.

The outer pipe 50 may comprise a sleeve having an elongated cylindrical body 60. For example, the outer pipe 50 may be a hollow right circular cylinder. The elongated cylindrical body 60 may be formed of metallic, plastic, or other suitable material operable to communicate variable stress conditions to a sample cement composition in the test chamber 56. In a particular embodiment, the elongated cylindrical body 60 comprises steel or other metal operable to readily communicate temperature changes from the pressure cell 40 to the sample cement composition in the test chamber 56. In another embodiment, the elongated cylindrical body 60 may comprise anodized aluminum, stainless steel, brass, and/or copper, such as a cylinder formed from an aluminum can with wall thickness between 3 and 6 mils ($1/1000$ of an inch). A thermocouple 122 (FIG. 3) may be attached to the outer pipe 50 or placed in the pressure cell 40.

The inner pipe 52 may comprise an elongated cylindrical body 70. For example, the inner pipe 52 may be a hollow right cylinder. In one embodiment, the elongated cylindrical body 70 may comprise stems 72 extending from an intermediate section 74 through the end caps 54. In particular, a top stem 72a may extend through the top end cap 54a and a bottom stem 72b may extend through the bottom end cap 54b. The intermediate section 74 may have a diameter enlarged from that of the stems 72 to, for example, more accurately simulating casing in a well bore, control the area of the test chamber 56 to which pressure and/or temperature changes are applied and/or to control dimensions of the test chamber 56. The stems 72 may each comprise external threads for coupling to a pipe, line or other suitable device. Other pressure tight connectors may be used. For example, clamps or quick connects may be used.

The elongated cylindrical body 70 may comprise metallic, plastic or other suitable material operable to expand and/or otherwise communicate variable stress conditions to the sample cement composition in the test chamber 56. In a particular embodiment, the elongated cylindrical body 70 may comprise PVC operable to communicate both pressure and temperature changes to the test chamber 56.

End caps 54 secure the inner pipe 52 in the outer pipe 50. In one embodiment, the end caps 54 each comprise a circular body 80 with a central orifice 81 through which the corresponding stem 72 of the inner pipe 52 extends. The central orifices 81 may be formed to maintain the inner pipe 52 concentrically within the outer pipe 50. In this embodiment, an inner wall 82 and an outer wall 84 of the test chamber 56 may be concentric. The end caps 54 may comprise steel, plastic or other suitable material.

The end caps 54 may be threaded onto or be otherwise fastened to the outer pipe 50. The end caps 54 may each include an outer seal 86 extending around the outer perimeter of the circular body 80 to provide a seal between the end cap 54 and the outer pipe 50. End caps 54 may also each include an inner seal 88 extending around the central orifice in circular body 80 to provide a seal between the end cap 54 and the stem 72 extending through the end cap 54. The outer seal 86 and inner seal 88 may each comprise O-rings or other suitable seals operable to form a pressure tight seal for the test chamber 56. In one embodiment, the test chamber 56 may be safely operated up to a pressure of 10,000 psi.

Ports 90 may be formed in each of the end caps 54 to allow fluid communication with the test chamber 56 during testing. For example, ports 90 provide a fluid inlet and outlet for sheath failure and other permeability change measurements. The ports 90 may also be used for cement shrinkage measurements by connection to a measuring device. The ports 90 may each comprise internal threads for connection to an external pipe, hose, line or other suitable device. Other pressure tight connectors may be used.

The test chamber 56 may be annular and, in a specific embodiment, have concentric inner and outer pipes 50 and 52. In this embodiment, the test chamber 56 may simulate the space of a well bore between a casing represented by the inner pipe 52 and a formation or outer casing represented by outer pipe 50. The test chamber 56 may otherwise provide a geometry similar to that expected downhole. In a particular embodiment, the test chamber 56 may have, for example, a length of between twelve (12) inches and twenty-four (24) inches, an outer diameter of three (3) to six (6) inches and an inner diameter of one (1) to four (4) inches. The test chamber 56 may be otherwise suitably configured, sized and shaped. For example, the test chamber 56 may have a length/diameter ratio of 3 to 12 and an outer diameter of 2 to 3 times the inner diameter.

A distributor 95 may be disposed at the bottom of the test chamber 56 in a notch formed in the elongated cylindrical body 60 of the outer pipe 50. The distributor 95 evenly, or substantially evenly, distributes fluid received from port 90 of the bottom end cap 54b across a base of the sample cement composition in the test chamber 56. In one embodiment, the distributor 95 comprises a mesh screen 96 and sand 98. The mesh screen 96 maintains the sand 98 in place. The screen 96 may, for example, comprise a 325-mesh screen. Other suitable screens 96 and high permeability materials may be used. In addition, other suitable structures may be used for distributor 95.

Sensors 100 may be mounted to the inside and/or outside of the outer pipe 50 and/or inner pipe 52 or otherwise suitably coupled to the test chamber 56. In one embodiment, the sensors 100 are small such that their effect on the geometry of the test cell 42 and the parameters they measure is minimal. In this and/or other embodiments, the sensors 100 may, for example, be placed such that during testing cement in the test chamber 56 covers the sensing area and extends at least one outer pipe 50 diameter below and above the location of the sensors 100. In a particular embodiment, the sensors 100 may be mounted to the outer pipe 50 and inner pipe 52 at the center of the test chamber 56 to reduce and/or minimize end effects at the bottom and top of the test chamber 56.

The sensors 100 are operable to sense and/or measure force, stress, strain and/or displacement from a sample cement composition which may include force, stress, strain and/or displacement from contact of the sensor and/or portions of the test chamber 56 with the sample cement composition. In one embodiment, the sensors 100 may measure any parameter from which contact stress can be calculated. The force, stress, strain, and/or displacement measurements may be the actual or an indication of the actual force, stress, strain, and/or displacement and/or a change in the same. The sensors 100 may comprise one or more contact stress sensors, force sensors, strain gauges and/or displacement sensors mounted to the inside or outside the test chamber 56. In a particular embodiment, contact stress or force sensors 102 may be mounted to the inner diameter of the outer pipe 50 and to the outer diameter of the inner pipe 52. In a particular embodiment, FLEXIFORCE contact stress sensors manufactured by TEKSCAN or other suitable thin film sensors may be used. In this and/or other embodiments, strain gauges or displacement sensors 104 may be mounted to the inner or outer diameter of the outer pipe 50 and to the inner or outer diameter of the inner pipe 52. The strain gages may, in one embodiment, comprise fiber optic systems to sense strains.

The sensors 100 may be covered with silicon, packaging or other suitable tape or otherwise suitably protected in the test cell 42. The sensors 100 may be connected by wire or otherwise suitably to the controller 26. For example, a wire (not shown) may extend from each sensor 100 through the top end cap 54a and be connected to the controller 26. The contact force or contact stress sensors 102 may be used without the strain gauges 104 and/or the strain gauges 104 used without the contact stress sensors 102. In addition, a single stress sensor 102 and/or strain gauge 104 may be used.

Figure 3:
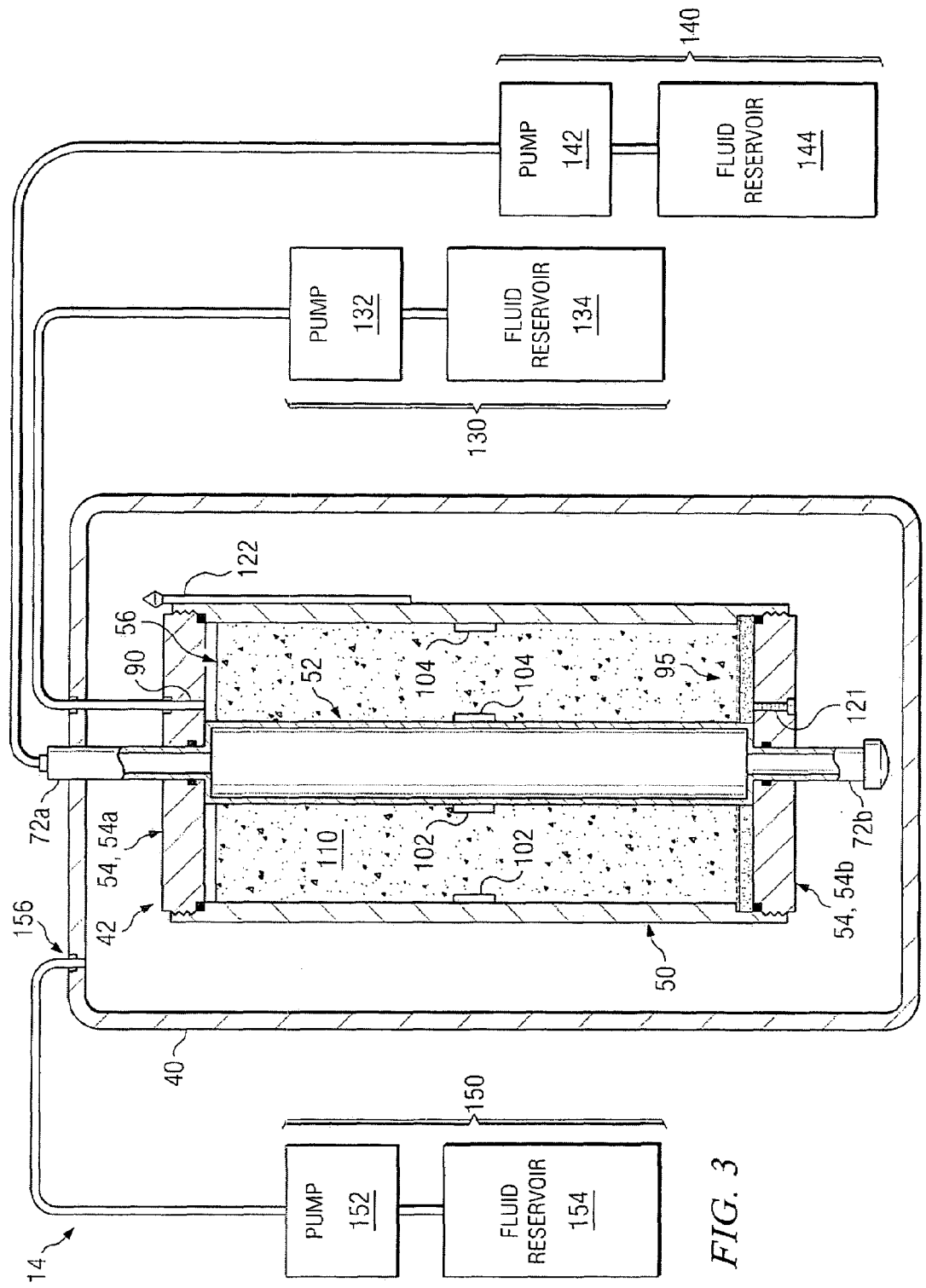
FIG. 3 is a diagram illustrating one embodiment of testing a sample cement composition using the test cell of FIG. 2.

In operation, the sand 104 may be saturated with water and a sample cement composition poured into the test chamber 56 for testing. The cement may be cured with or without a water cap on top of the sample cement composition. The sealed test cell assembly 42 with the sample cement composition may be secured in the pressure cell 40 of the test assembly 14 and the inner pipe 52 connected to variable pressure and/or temperature systems capable of varying pressure and/or temperature applied to the sample cement composition. Means to sense sheath failure, cement shrinkage, mechanical property and/or other test equipment may be connected to ports 90 for the test. FIG. 3 illustrates an embodiment of a test for a sample cement composition using the test cell 42.

FIG. 3 illustrates one embodiment of a test for a sample cement composition 110 using the test cell 42. In this embodiment, the test cell 42 is set up and the sample cement composition 110 poured into the test cell 42 as previously described. Accordingly, the sample cement composition 110 will have an annular form. The test cell 42 is secured in the pressure cell 40 to form the test assembly 14. Although not shown in FIG. 3, the test assembly 14 may be secured in the laboratory apparatus 10 for testing. Alternatively, the test assembly 14 may be a stand alone device.

Referring to FIG. 3, the test chamber 56 is connected to a fluid pump system 130. The fluid pump system comprises a pump 132 and a fluid reservoir 134. The pump 132 may comprise a positive pressure or volume control pump such as, for example, an ISCO pump manufacture by TELEDYNE ISCO, Inc. of Lincoln, Nebr. The fluid pump system 130 may comprise other or different suitable equipment. The pump may in another embodiment, for example, comprise an intensifier or other device operable to raise, lower and/or control pressure in the pressure cell 40. The fluid pump system 130 may be connected to and controlled by controller 26.

In one embodiment, the port 90 of the top end cap 54*a* is connected to an outlet of pump 132. An inlet of pump 132 is connected to an outlet of fluid reservoir 134. The fluid may be oil or other suitable fluid. All connections between the pump 132, port 90 of the top end cap 54*a* and fluid reservoir 134 may be by fluid and/or pressure tight piping and connectors. The port 90 and the bottom end cap 54*b* may be plugged with plug 121. A thermocouple 122 may be secured in the pressure cell 40 to the outer pipe 50. The thermocouple 122 may be connected to the controller 26 of the laboratory apparatus 10.

In another embodiment the fluid pump system 130 may be omitted and a pipette may be connected to the port 90 of the top end cap 54*a*. The pipette may contain dyed liquid and be graduated to allow fluid level changes to be easily monitored during curing of the sample cement composition 110 to determine cement shrinkage. In still another embodiment, the fluid pump system 130 may be omitted with the sample cement composition 110 exposed to pressure of the pressure cell 40 during curing and/or later testing.

Inner pipe 52 is connected to a variable pressure system 140. The variable pressure system 140 may comprise a pump 142 and a fluid reservoir 144. As previously described in connection with pump 132, pump 142 may comprise a positive pressure or volume control pump such as an ISCO pump or other suitable device. In a particular embodiment, the top stem 72*a* of the inner pipe 52 is connected to an outlet of the pump 142. An inlet of the pump 142 is connected to an outlet of the fluid reservoir 144. The fluid may be oil, water, or other suitable fluid. The bottom stem 72*b* of the inner pipe 52 is capped. All connection may be by fluid and/or pressure tight piping and connectors. Fluid may be pumped to and from the inner pipe 52 by pump 142 to vary or otherwise control pressure. The variable pressure system 140 may comprise other or different suitable equipment for generating pressure. The variable pressure system 140 may be connected to and controlled by controller 26.

In another embodiment, the variable pressure system 140 may circulate water through the inner pipe 52 to control temperature as well as pressure in the inner pipe 52. In this embodiment, the fluid reservoir 144 may have in inlet connected to the bottom stem 72*b* of the inner pipe 52 and may be heated or cooled to vary and otherwise control temperature in the inner pipe 52. A back pressure valve or other circulation and pressure control device may be installed on the bottom stem 72*b* of inner pipe 52 and the pump 142 used to vary temperature and pressure in the inner pipe 52.

Pressure cell 40 is connected to a variable pressure system 150. The variable pressure system 150 may comprise a pump 152 and a fluid reservoir 154. As previously described in connection with pumps 132 and 142, pump 152 may comprise a positive pressure or volume control pump such as an ISCO pump or other suitable device. In a particular embodiment, a port 156 of the pressure cell 40 is connected to an outlet of the pump 152. An inlet of the pump 152 is connected to an outlet of the fluid reservoir 154. The fluid may be oil or other suitable fluid. All connections may be by fluid and/or pressure tight piping and connectors. Fluid may be pumped to and from the pressure cell 40 to vary or otherwise control pressure. The variable pressure system 150 may comprise other or different suitable equipment for generating pressure. The variable pressure system 150 may be connected to and controlled by controller 26.

In the illustrated embodiment, the fluid pump system 130 and variable pressure system 140, as well as the variable pressure system 150 of the pressure cell 40 form the variable stress system operable to apply temperature and pressure changes to the sample cement composition 110 in the test chamber 56. Thus, the variable stress system may comprise one or several distinct systems and may be any device or set of devices coupled to the test cell 42 to heat, cool, pressurize, depressurize and/or otherwise control conditions for testing concrete for a well bore. The variable stress system may adjust, change, increase, decrease and/or otherwise control pressure and/or temperature applied to the sample cement composition 110 in the test chamber 56.

In response to the changes, the sensors 100, as described in more detail below, measure stresses, strains and/or displacements from the sample cement composition 110. As used herein, in response to an identified event means in response to at least the identified event. Accordingly, necessary or other intervening events may occur between the indicated event and action.

During curing, curing pressure and/or temperature are applied to the sample cement composition 110 in the test chamber 56. In one embodiment, the curing pressure is applied to the test chamber 56 through the outer pipe 50 and inner pipe 52. In another embodiment, pressure and/or a pressure differential may be applied to the sample cement composition in the test chamber via ports 90 in the top and bottom end caps 54. The curing temperature may also be applied to the test chamber 56. The curing pressure and temperature may be the temperature and pressure expected in the well bore for which the sample cement composition 110 is being tested.

While maintaining and/or providing curing temperature and pressure, the sample cement composition 110 is allowed to cure for a specified time. During curing, the volume added or taken out of the test chamber 56 to maintain a constant pressure is measured and recorded by the pump 132. In addition, contact stresses between the sample cement composition 110 and the inner and outer pipes 50 and 52 from the sample cement composition 110 are measured by the stress sensors 102 and recorded by controller 26. Strains in the inner and outer pipes 50 and 52 are measured by strain gauges 104 and recorded by controller 26. The data may be measured and/or recorded continuously, or periodically. For example, data points may be stored once each second, several times each second, or once every few seconds, or, for example, minutes. The change in contact stresses and/or pipe strains during curing of the sample cement composition 110 may be used to rate the sample cement composition's 110 ability to maintain the as-placed stress state, which in turn may be used to determine the potential for a micro annulus to form in the sample cement composition 110 during the well's life. The as-placed stress state may, for example, be determined based on the strength and/or duration of the seal formed by the sample cement composition and/or using a model or other predictor based on measured values. The model may predict the change in stress and contact stress with change in applied load.

After the sample cement composition 110 has cured, the pressure in the inner pipe 52 is varied and the changes in contact stresses and/or pipe strains in the inner and outer pipes 50 and 52 induced, caused or otherwise in response to the change in internal pressure are measured and recorded by controller 26. In one embodiment, the pressure in the inner pipe 52 is incremented in one or more steps. For example, during curing, the pressure in the inner pipe 52 may be the curing pressure and the pressure incremented in steps of 50 psi for three (3) or four (4) steps or up to the pressure rating for the test cell 42. In another specific embodiment, pressure may be incremented from 0 psi to 50 psi to 100 psi and finally to 150 psi. In an embodiment in which the inner and outer pipes 50 and 52 of the test cell 42 comprise steel, the pressure may be raised, for example, up to 1000 psi or until the cement cracks. For a PVC embodiment, pressure may, for example, be raised to 100 psi. In some embodiments, a single pressure change or increment may be used. In other embodiments, pressure may be raised at a pre-determined rate.

Upon the completion of testing or otherwise suitably, the Young's modulus and Poisson's ratio of the sample cement composition 110 may be determined from changes in stress and/or pipe strains measured and/or recorded during the testing. The Young's modulus is a material property that describes the stiffness or elasticity of the sample cement composition 110. Poisson's ratio is a ratio of traverse contraction or expansion strain to longitudinal extension or compaction strain in the direction of stretching or compaction force. In one embodiment where changes in contact stresses are measured, Young's modulus and Poisson's ratio are determined from the change in contact stresses measured for a known pressure change in the inner pipe 52. Internal pressure applied is equal to the net change in pressure. The resulting contact stress change for applied pressure may be determined by subtracting the initial contact stress value (prior to the application of the internal pressure) from the final contact stress value. Where i indicates region (i=0 for inside the inner pipe 52, i=1 for the inner pipe 52, i=2 for the cement sheath formed by the sample cement composition 110 in the test chamber 56, and i=3 for the outer pipe 50), P indicates pressure at the outer diameter of region i, $a_i$ indicates inner radius for region i, $b_i$ indicates outer radius for region i and $I_i$ and $\theta_i$ are mechanical properties of each medium which can be related back to Young's modulus ($E_i$) and Poisson's ratio ($v_i$) using $\alpha_i=(1-2v_i)\beta_i$ and $\beta_i=1+v_i/E_i$, Young's modulus and Poisson's ratio may be determined as follows where the two relevant interfaces between the inner pipe 52 and the cement sheath and between the cement sheath and the outer pipe 50 remain in intimate contact ($a_i:=b_1$ and $b_2:=a_3$) at all times and the inner and outer pipes 50 and 52 are made of the same material ($\alpha_3=\alpha_1$ and $\beta_3=\beta_1$). X and Y vectors, which are constants relating to the geometry of the system, may be determined as follows:

$$X := \left[ \frac{a_1^2}{b_1^2 - a_1^2}, \frac{b_1^2}{a_3^2 - b_1^2}, \frac{a_3^2}{b_3^2 - a_3^2} \right]$$

$$Y := \left[ \frac{b_1^2}{b_1^2 - a_1^2}, \frac{a_3^2}{a_3^2 - b_1^2}, \frac{b_3^2}{b_3^2 - a_3^2} \right]$$

Using the X and Y vectors, constants A and B may thereafter be defined as follows:

$$A := \left[ \frac{1}{2} \frac{b_1^2 P_1 - a_1^2 P_0}{b_1^2 - a_1^2}, \frac{1}{2} \frac{-a_3^2 P_2 + b_1^2 P_1}{-a_3^2 + b_1^2}, \frac{1}{2} \frac{-b_3^2 P_3 + a_3^2 P_2}{-b_3^2 + a_3^2} \right]$$

$$B := \left[ \frac{a_1^2 b_1^2 (P_0 - P_1)}{b_1^2 - a_1^2}, \frac{b_1^2 a_3^2 (P_1 - P_2)}{a_3^2 - b_1^2}, \frac{a_3^2 b_3^2 (P_2 - P_3)}{b_3^2 - a_3^2} \right]$$

The initial outer diameter circumferences may be determined as follows:

$OD\_circ\_0:=[2\pi b_1, 2\pi a_3, 2\pi b_3]$

Using constants A and B and solving for displacements at the region inner diameter (u_r_id) and outer diameter (u_r_od) locations provides:

$$u\_r\_id := \left[ \frac{\alpha_1(b_1^2 P_1 - a_1^2 P_0)a_1}{b_1^2 - a_1^2} - \frac{\beta_1 a_1 b_1^2 (P_0 - P_1)}{b_1^2 - a_1^2}, \right.$$
$$\frac{\alpha_2(-a_3^2 P_2 + b_1^2 P_1)b_1}{-a_3^2 + b_1^2} - \frac{\beta_2 b_1 a_3^2 (P_1 - P_2)}{a_3^2 - b_1^2},$$
$$\left. \frac{\alpha_1(-b_3^2 P_3 + a_3^2 P_2)a_3}{-b_3^2 + a_3^2} - \frac{\beta_1 a_3 b_3^2 (P_2 - P_3)}{b_3^2 - a_3^2} \right]$$

$$u\_r\_od := \left[ \frac{\alpha_1(b_1^2 P_1 - a_1^2 P_0)b_1}{b_1^2 - a_1^2} - \frac{\beta_1 a_1^2 b_1 (P_0 - P_1)}{b_1^2 - a_1^2}, \right.$$
$$\frac{\alpha_2(-a_3^2 P_2 + b_1^2 P_1)a_3}{-a_3^2 + b_1^2} - \frac{\beta_2 b_1^2 a_3 (P_1 - P_2)}{a_3^2 - b_1^2},$$
$$\left. \frac{\alpha_1(-b_3^2 P_3 + a_3^2 P_2)b_3}{-b_3^2 + a_3^2} - \frac{\beta_1 a_3^2 b_3 (P_2 - P_3)}{b_3^2 - a_3^2} \right]$$

Using displacements at the region inner diameter (ID) and outer diameter (OD) and solving for cement mechanical properties when the ID of the cement sheath is equal to the OD of inner pipe 52 and the ID of the outer pipe 50 is equal to the OD of the cement sheath provides:

MechProp_CP:={$\alpha_2 = (-P_1 b_1^4 b_3^2 \alpha_1 + P_1 b_1^4 \alpha_1 a_3^2 - b_1^2 P_1 b_3^2 \beta_1 a_1^2 + b_1^2 P_1 \beta_1 q a_1^2 a_3^2 - b_1^2 a_3^4 \alpha_1 P_2 a_3^2 {}_1^2 \beta_1 b_3^2 P_3 a_3^4 \alpha_1^2 \alpha_1 P_2 - b_1^2 a_3^2 P_2 \beta_1 b_3^2 - a_3^2 a_1 \alpha_1 b_3^2 P_3 + b_1^2 {}_3^2 \alpha_1 b_3^2 P_3 + a_3^2 P_2 a_1^2 \beta_1 b_3^2 + b_1^2 b_3^2 \alpha_1 a_1^2 P_0 + b_1^2 b_3^2 \beta_1 a_1^2 P_0 + b_1^2 a_3^2 \beta_1 b_3^2 P_3 - b_1^2 \alpha_1 a_1^2 P_0 a_3^2 - b_1^2 \beta_1 a_1^2 P_0 a_3^2)/ ((a_1^2 b_3^2 - a_3^2 b_1^2 + a_3^2 a_1^2 a_3^2)(-a_3^2 P_2 + b_1^2 P_1))$, $\beta_2 = -(-b_1^2 b_3^2 \alpha_1 P_1 \beta_1 a_1^2 P_1 a_3^2 \alpha_1 b_3^2 P_3 b_1^2 + \alpha_1 b_1^2 P_1 a_3^2 \alpha_1 a_3^2 P_2 b_1^2 - \beta_1 b_3^2 P_2 b_1^2 + \beta_1 b_3^2 P_3 b_1^2 - a_1^2 \alpha_1 b_3^2 P_3 + b_3^2 \alpha_1 a_1^2 P_0 + b_3^2 \beta_1 a_1^2 P_0 - b_3^2 \beta_1 a_1^2 P_1 - \alpha_1 a_1^2 P_0 a_3^2 - \beta_1 a_1^2 P_0 a_3^2 {}_1 - \beta_1 a_1^2 P_0 a_3^2 - a_1^2 \beta_1 b_3^2 P_3 + a_1^2 \alpha_1 a_3^2 P_2 + a_1^2 \beta_1 b_3^2 P_{2})(-b_1^2 P_1 b_3^2 + a_3^2 P_2 a_1^2 P phd 2b_1^2 + a_1^2 P_1 b_3^2 a_1^2 P_2 b_3^2 + b_1^2 P_1 a_3^2 + b_3^2 P_2 b_1^2 - aq_1^2 P_1 a_3^2)$}, $\alpha_2 := (-P_1 b_1^4 b_3^2 \alpha_1 + P_1 b_1^4 \alpha_1 a_3^2 - b_1^2 P_1 b_3^2 \beta_1 a_1^2 + b_1^2 P_1 \beta_1 a_1 a_3^2 - b_1^2 a_3^4 \alpha_1 P_2 - b_1^2 a_3^4 \alpha_1 P_2 - a_3^2 a_1^2 \beta_1 b_3^2 P_3 + a_3^4 a_1^2 \alpha_1 P_2 - b_1^2 a_3^2 P_2 \beta_1 b_3^2 - a_3^2 a_1^2 \alpha_1 b_3^2 P_3 + b_1^2 a_3^2 \alpha_1 b_3^2 P_3 + a_3^2 P_2 a_1^2 \beta_1 b_3^2 + b_1^2 b_3^2 \alpha_1 a_1^2 P_0 + b_1^2 b_3^2 \beta_1 a_1^2 P_0 + b_1^2 a_3^2 \beta_1 b_3^2 P_3 - b_1^2 \alpha_1 a_1^2 P_0 a_3^2 - b_1^2 \beta_1 a_1^2 P_0 a_3^2)/((b_3 - a_3)(b_3 + a_3)(-b_1 + a_1)(a_1 + b_1)(-a_3^2 P_2 + b_1^2 P_1))$ $\beta_2 := -(-b_1^2 b_3^2 \alpha_1 P_1 + \beta_1 a_1^2 {}_1 a_3^2 + \alpha_1 b_3^2 P_3 b_1^2 \alpha_1 b_1^2 P_1 a_{32} - \alpha_1 a_3^2 P_2 b_1^2 - \beta_1 b_3^2 P_2 b_1^2 + \beta_1 b_3^2 P_3 bphd 1^2 - a_1^2 \alpha_1 b_3^2 P_3 + b_3^2 \alpha_1 a_1^2 P_0 + b_3^2 \beta_1 a_2 P_0 - b_3^2 \beta_1 a_1^2 P_1 - \alpha_1 a_1^2 P_0 a_3^2 \beta_1 a\, m_1^2 P_0 a_3^2 - a_1^2 \beta_1 b_3^2 P_3 + a_1^2 \alpha_1 a_3^2 P_2 + a_1^2 \beta_1 b_3^2 P_2)/((-b_3 + a_3)(b_3 + a_3)(b_1 - a_1)(a_1 + b_1)(P_1 - P_2))$ For the cement sheath, using $$\alpha_2 = (1 - 2v_2)\beta_2,$$

$$\beta_2 = \frac{1 + v_2}{E_2}$$

and the above mechanical properties, Young's modulus and Poisson's ratio may be determined from the following equations:

$$v_2 = \frac{\beta_2 - \alpha_2}{2\beta_2}$$

-continued $$E_2 = \frac{3\beta_2 - \alpha_2}{2\beta_2^2}$$

In another embodiment, where changes in strains of the inner and outer pipe 50 and 52 OD are measured, Young's modulus and Poisson's ratio for the sample cement composition 110 may be determined from the change in strains measured for a known pressure change in the inner pipe 52. Internal pressure applied is equal to the net change in pressure. The resulting stress change for the pressure may be determined by subtracting the initial stress value (prior to application of the internal pressure) from the final stress value. Using the previously defined X and Y vectors, constants A and B, the initial OD circumferences and displacements of region ID and OD, Young's modulus and Poisson's ratio may be determined as follows where the two relevant interfaces between the inner pipe 52 and the cement sheath and between the cement sheath and the outer pipe 50 remain in intimate contact at all times and the inner and outer pipes 50 and 52 are made of the same material. Using displacements at region ID and OD locations provides final system dimensions for the inner radius (a_f), outer radius (b_f), OD circumference (OD_circ_f) and OD strains (OD_strain) as follows:

$$a\_f := \left[ a_1 - \frac{2\alpha_1(b_1^2 P_1 - a_1^2 P_0)a_1}{b_1^2 - a_1^2} + \frac{2\beta_1 a_1 b_1^2(P_0 - P_1)}{b_1^2 - a_1^2}, \right.$$

$$b_1 - \frac{2\alpha_2(-a_3^2 P_2 + b_1^2 P_1)b_1}{-a_3^2 + b_1^2} + \frac{2\beta_2 b_1 a_3^2(P_1 - P_2)}{a_3^2 + b_1^2},$$

$$\left. a_3 - \frac{2\alpha_1(-b_3^2 P_3 + a_3^2 P_2)a_3}{-b_3^2 + a_3^2} + \frac{2\beta_1 a_3 b_3^2(P_2 - P_3)}{b_3^2 - a_3^2} \right]$$

$$b\_f := \left[ b_1 - \frac{2\alpha_1(b_1^2 P_1 - a_1^2 P_0)b_1}{b_1^2 - a_1^2} + \frac{2\beta_1 a_1^2 b_1(P_0 - P_1)}{b_1^2 - a_1^2}, \right.$$

$$a_3 - \frac{2\alpha_2(-a_3^2 P_2 + b_1^2 P_1)a_3}{-a_3^2 + b_1^2} + \frac{2\beta_2 b_1^2 a_3(P_1 - P_2)}{a_3^2 - b_1^2},$$

$$\left. b_3 - \frac{2\alpha_1(-b_3^2 P_3 + a_3^2 P_2)b_3}{-b_3^2 + a_3^2} + \frac{2\beta_1 a_3^2 b_3(P_2 - P_3)}{b_3^2 - a_3^2} \right]$$

$$OD\_circ\_f := \left[ 2\pi \left( b_1 - \frac{2\alpha_1(b_1^2 P_1 - a_1^2 P_0)b_1}{b_1^2 - a_1^2} + \frac{2\beta_1 a_1^2 b_1(P_0 - P_1)}{b_1^2 - a_1^2} \right), \right.$$

$$2\pi \left( a_3 - \frac{2\alpha_2(-a_3^2 P_2 + b_1^2 P_1)a_3}{-a_3^2 + b_1^2} + \frac{2\beta_2 b_1^2 a_3(P_1 - P_2)}{a_3^2 - b_1^2} \right),$$

$$\left. 2\pi \left( b_3 - \frac{2\alpha_1(-b_3^2 P_3 + a_3^2 P_2)b_3}{-b_3^2 + a_3^2} + \frac{2\beta_1 a_3^2 b_3(P_2 - P_3)}{b_3^2 - a_3^2} \right) \right]$$

$$OD\_strains := \left[ \frac{1}{2} \frac{2\pi \left( b_1 - \frac{\frac{2\alpha_1(b_1^2 P_1 - a_1^2 P_0)b_1}{b_1^2 - a_1^2} +}{\frac{2\beta_1 a_1^2 b_1(P_0 - P_1)}{b_1^2 - a_1^2}} \right) - 2\pi b_1}{\pi b_1}, \right.$$

$$\frac{1}{2} \frac{2\pi \left( a_3 - \frac{\frac{2\alpha_2(-a_3^2 P_2 + b_1^2 P_1)a_3}{-a_3^2 + b_1^2} +}{\frac{2\beta_2 b_1^2 a_3(P_1 - P_2)}{a_3^2 - b_1^2}} \right) - 2\pi a_3}{\pi a_3},$$

$$\frac{1}{2} \frac{2\pi \left( b_3 - \frac{\frac{2\alpha_1(-b_3^2 P_3 + a_3^2 P_2)b_3}{-b_3^2 + a_3^2} +}{\frac{2\beta_1 a_3^2 b_3(P_2 - P_3)}{b_3^2 - a_3^2}} \right) - 2\pi b_3}{\pi b_3} \Bigg]$$

Using final system dimensions, contact stresses (P_contact) may be determined from the measured strains as follows:

$$P\_Contact := \left\{ P_2 = \frac{1}{2} \frac{-2\alpha_1 b_3^2 P_3 - 2\beta_1 a_3^2 P_3 - mstrain_3 b_3^2 + mstrain_3 a_3^2}{a_3^2(\alpha_1 + \beta_1)}, \right.$$

$$\left. P_1 = \frac{1}{2} \frac{-2\alpha_1 a_1^2 P_0 - 2\beta_1 a_1^2 P_0 + mstrain_1 b_1^2 - mstrain_1 a_1^2}{\alpha_1 b_1^2 + \beta_1 a_1^2} \right\}$$

$$P_1 := \frac{1}{2} \frac{-2\alpha_1 a_1^2 P_0 - 2\beta_1 a_1^2 P_0 + mstrain_1 b_1^2 - mstrain_1 a_1^2}{\alpha_1 b_1^2 + \beta_1 a_1^2}$$

$$P_2 := \frac{1}{2} \frac{-2\alpha_1 b_3^2 P_3 - 2\beta_1 a_3^2 P_3 - mstrain_3 b_3^2 + mstrain_3 a_3^2}{a_3^2(\alpha_1 + \beta_1)}$$

Using the contact stresses for cement and solving for cement mechanical properties where the ID of the cement sheath is equal to the OD of inner pipe 52 and the ID of the outer pipe 50 is equal to the OD of the cement sheath provides:

MechProp_CP:{$\beta_2 = -(b_1^2 a_3^2 mstrain_1 \alpha_1^2 - 2\alpha_1^2 b_3^2 \beta_1 P_3 b_1^2 - \beta_1 b_3^2 mstrain_3 \alpha_1 b_1^2 - b_1^2 a_3^2 \alpha_1^2 mstrain_3 + 2 b_1^2 a_3^2 \alpha_1^2 \beta_1 P_3 + b_1^2 \alpha_1 a_3^2 mstrain_1 \beta_1 + 2 a_3^2 \alpha_1 \beta_1^2 P_3 a_1^2 \beta_1^2 b_3^2 mstrain_3 a_1^2 - 2\alpha_1 b_3^2 \beta_1^2 P_3 a_1^2 + a_1^2 a_3^2 mstrain_1 \beta_1 + \beta_1^2 a_1^2 a_3^2 mstrain_1 - a_3^2 \alpha_1 mstrain_3 \beta_1 a_1^2)/(-2 a_3^2 \alpha_1^2 a_1^2 P_0 - 4 a_3^2 \alpha_1 a_1^2 P_0 \beta_1 - 2 a_3^2 \beta_1^2 a_1^2 P_0 + a_3^2 mstrain_1 b_1^2 \alpha_1 + a_3^2 mstrain_1 b_1^2 \beta_1 - a_3^2 mstrain_1 a_1^2 \alpha_1 - a_3^2 mstrain_1 a_1^2 \beta_1 + 2\alpha_1^2 b_3^2 P_3 b_1^2 + 2\alpha_1 b_3^2 P_3 \beta_1 a_1^2 + 2\beta_1 a_3^2 P_3 \alpha_1 b_1^2 + 2\beta_1^2 a_3^2 P_3 a_1^2 + mstrain_3 b_3^2 \alpha_1 b_1^2 + mstrain_3 b_3^2 \beta_1 a_1^2 - mstrain_3 a_3^2 \alpha_1 b_1^2 - mstrain_3 a_3^2 \beta_1 a_1^2$), $\alpha_2 = (-2\alpha_1^2 b_3^2 \beta_1 P_3 b_1^2 - \beta_1 b_3^2 mstrain_3 \alpha_1 b_1^2 - b_1^2 a_3^2 \alpha_1^2 mstrain_3 + 2 b_1^2 a_3^2 \alpha_1 \beta_1 P_3 2 a_3 \alpha_1 \beta_1^2 P_3 a_1^2 - \beta_1^2 b_3^2 mstrain_3 a_1^2 - 2\alpha_1 b_3^2 \beta_1^2 P_3 a_1^2 - a_1^2 \alpha_1 mstrain_3 \beta_1 a_1^2 + b_1^4 \alpha_1 mstrain_1 \beta_1 + b_1^2 a_1^2 \alpha_1 mstrain_1 + \beta_1^2 a_1^2 b_1^2 mstrain_1 + b_1^4 mstrain_1 \alpha_1^2)/(2\alpha_1^2 b_3^2 P_3 b_1^2 + 2\alpha_1 b_3^2 P_3 \beta_1 a_1^2 + 2\beta_1 a_3^2 P_3 \alpha_1 b_1^2 + 2\beta_1^2 a_3^2 P_3 a_1^2 + mstrain_3 b_3^2 \alpha_1 b_1^2 + mstrain_3 b_3^2 \beta_1 a_1^2 - mstrain_3 a_3^2 \alpha_1 b_1^2 - mstrain_3 a_3^2 \beta_1 a_1^2 - 2 b_1^2 \alpha_1^2 a_1^2 P_0 - 4 b_1^2 \alpha_1 a_1^2 P_0 \beta_1 - 2 b_1^2 \beta_1^2 a_1^2 P_0 + b_1^4 mstrain_1 \alpha_1 + b_1^4 mstrain_1 \beta_1 - b_1^2 mstrain_1 a_1^2 \alpha_1 - b_1^2 mstrain_1 a_1^2 \beta_1$)}

$\alpha_2 := -(\alpha_1 b_1^2 + \beta_1 a_1^2)(-2\beta_1 \alpha_1 b_3^2 P_3 + 2\beta_1 a_3^2 P_3 \alpha_1 - \beta_1 b_3^2 mstrain_3 + mstrain_1 b_1^2 \beta_1 + mstrain_1 b_1^2 \alpha_1 - mstrain_3 a_3^2 \alpha_1)/(-b_1^4 mstrain_1 \alpha_1 - mstrain_3 b_3^2 \beta_1 a_1^2 + mstrain_3 a_3^2 \beta_1 a_1^2 - 2\alpha_1 b_3^2 P_3 \beta_1 a_1^2 - 2\beta_1^2 a_3^2 P_3 a_1^2 + mstrain_3 a_3^2 \alpha_1 b_1^2 - 2\beta_1 a_3^2 P_3 \alpha_1 b_1^2 + 2 b_1^2 \alpha_1^2 a_1^2 P_0 - b_1^4 mstrain_1 \beta_1 - 2\alpha_1^2 b_3^2 P_3 b_1^2 mstrain_3 b_3^2 \alpha_1 b_1^2 + 4 b_1^2 \alpha_1 a_1^2 P_0 \beta_1 + 2 b_1^2 \beta_1^2 a_1^2 P_0 + b_1^2 mstrain_1 a_1^2 \alpha_1 + b_1^2 mstrain_1 a_1^2 \beta_1)$ $\beta_2 := -(\alpha_1 b_1^2 + \beta_1 a_1^2)(2\beta_1 \alpha_1 b_3^2 P_3 - 2\beta_1 a_3^2 P_3 \alpha_1 - a_3^2 mstrain_1 \alpha_1 + mstrain_3 a_3^2 60_1 + \beta_1 b_3^2 mstrain_3 - a_3^2 mstrain_1 \beta_1)/(-mstrain_3 b_3^2 \beta_1 a_1^2 - 2\beta_1^2 a_3^2 P_3 a_1^2 + 2 a_3^2 \beta_1^2 a_1^2 P_0 + a_3^2 mstrain_1 a_1^2 \alpha_1 + mstrain_3 a_3^2 \beta_1 a_1^2 + 2 a_3^2 \alpha_1^2 a_1^2 P_0 + 4 a_3^2 \alpha_1 a_1^2 P_0 \beta_1 + a_3^2 mstrain_1 a_1^2 \beta_1 - 2\alpha_1 b_3^2 P_3 \beta_1 a_1^2 - 2\beta_1 a_3^2 P_3 \alpha_1 b_1^2 + mstrain_3 a_3^2 \alpha_1 b_1^2 -$ $a_3^2 \text{mstrain}_1 b_1^2 \beta_1 - a_3^2 \text{mstrain}_1 b_1^2 \alpha_1 - 2\alpha_1^2 b_3^2 P_3 b_1^2 - \text{mstrain}_3 b_3^2 \alpha_1 b_1^2)$ For the cement sheath, Young's modulus and Poisson's ratio may be determined from the previously provided equations.

Similar equations may be derived for strain sensors 104 placed on the ID of both inner and outer pipes 50 and 52 or any combination of strain sensor locations on the inner and outer pipes 50 and 52. Where the inner and outer pipes 50 and 52 comprise disparate materials, Young's modulus and Poisson's ratio may be determined from measured stresses or strains by specifying the specific characteristics of the disparate materials. If only one contact stress or strain measurement is available, in one embodiment on the inner pipe 52, Young's modulus of the cement sheath can be estimated from the stress or strain measurements using an assumed value for Poisson's ratio for the sample cement composition 110. In one embodiment, a range for Poisson's ratio for cement may be of 0.2 to 0.3.

Once the Young's modulus of the sample cement composition 110 has been determined, the cement sheath tensile strength can be established by increasing the pressure in the inner pipe 52 until one or more tensile fractures are induced in the cement sheath. The onset of cracking can be determined by monitoring the contact stresses and/or pipe strains and observing an abrupt change in measurements (for example, a drop in pressure with accompanying increase in strains), applying a pressure differential between the top and bottom of the cement sheath and observing the onset of fluid flow between the high and low pressure regions using a dyed liquid, catch container or the like or monitoring acoustic emissions from the cement sheath. Where the contact stresses and/or pipe strains are measured, the tensile strength at the point of fracture initiation may be determined from the contact stresses and the internal pressure using the hoop stress equation.

In addition, in one embodiment, using the above methodology and equations and assuming Poisson's ratio, the mechanical properties of the cement sheath in a well bore can be determined on an instrumented casing string in a well once the cement sheath has cured. In one embodiment, the casing string on the ID of the cement sheath may be instrumented with contact force sensors and/or strain gauges prior to running in hole with data communicated to the surface for monitoring and analysis to determine the mechanical properties after cementing and curing.

Figure 4:
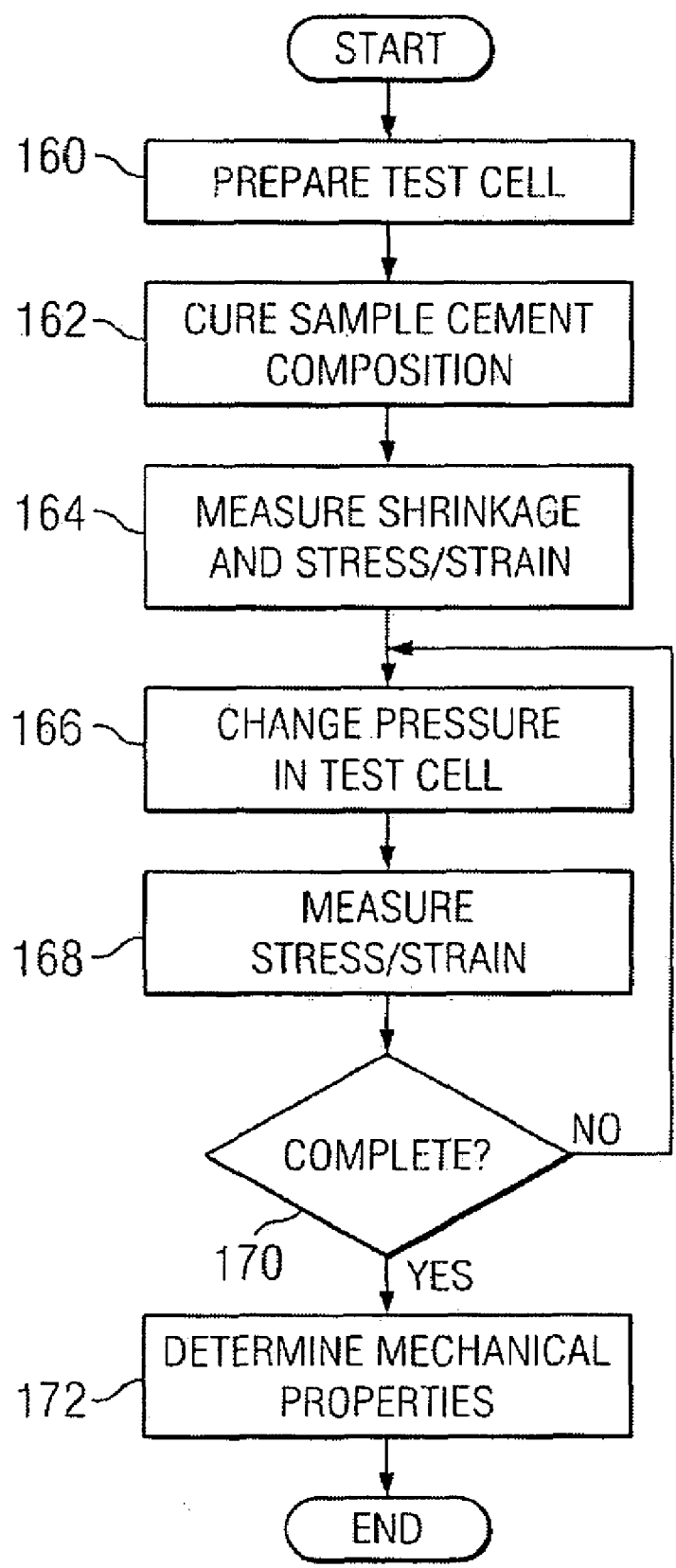
FIG. 4 is a flow diagram illustrating one embodiment of a method for testing mechanical properties of cement composition for a well bore.

FIG. 4 illustrates one embodiment of a method for determining mechanical properties of a sample cement composition 110. In one embodiment, full mechanical characterization may be provided. The method begins at step 160, in which the test cell 42 is prepared. Test cell 42 may be prepared as previously described by pouring the sample cement composition 110 into the test cell 42, providing a water cap and sealing the test cell 42. In width of the annular region in the test cell 42 and the material properties and dimensions of the inner and outer pipes 50 and 52 are known. The sealed test cell 42 may be placed in the laboratory apparatus 10 for testing.

At step 162, the sample cement composition 110 is cured. The sample cement composition 110 may be cured at a curing pressure and temperature using the pressure cell 40, fluid pump system 130, variable pressure system 140 and/or variable pressure system 150 of the laboratory apparatus 10. In one embodiment, a constant pressure may be maintained above and below the sample cement composition during curing. In a particular embodiment, the outer pipe 50, inner pipe 52 and sample cement composition 110 may all be exposed to a same confining pressure during curing, for example, 3000 psi, to simulate downhole conditions.

At step 164, during curing, the volume of fluid added or taken out of the test cell 42 to maintain a constant pressure is determined to measure shrinkage. Also during curing, contact stresses between the sample cement composition 110 and the inner and outer pipes 50 and 52 and/or the strains in the inner and outer pipes 50 and 52 are measured and recorded by controller 26. As previously described, the change in contact stresses and/or pipe strains observed during curing may be used to rate the cement's ability to maintain the as-placed stress state. In another embodiment, the outer pipe 50, inner pipe 52 and sample cement composition 110 may all be exposed to pressure of the pressure cell 40 during curing. In this embodiment, the fluid pump system 130 may be omitted and the variable pressure system 140 connected and/or used only after curing.

Proceeding to step 166, pressure is incremented or otherwise changed in the test cell 42. In one embodiment, pressure is incremented by incrementing pressure in the inner pipe 52. In this embodiment, pressure in the pressure cell 40 may be maintained constant at, for example, the curing pressure. At step 168, the change in contact stress between the cement sheath and the inner and outer pipes 50 and 52 and/or the strains induced in the inner and outer pipes 50 and 52 by changes in pressure are measured and recorded by controller 26. Also, a pressure differential may be established across the sample cement composition 110 to evaluate cement sheath permeability and/or determine if and under what conditions the cement sheath leaks.

At decisional step 170, if testing is not complete, the No branch returns to step 166 where the pressure is further incremented or changed for additional measurements at step 168. Thus, in one embodiment, the sample cement composition 110 may not be exposed to atmospheric conditions until after testing has been completed. Upon completion of testing at step 170, the Yes branch leads to step 172. At step 172, the mechanical properties of the sample cement composition 110 are determined for the known inner pipe 52 internal pressure changes as previously described. In particular, Young's modulus and Poisson's ratio, as well as the tensile strength, may be determined as previously described. Step 172 leads to the end of the process.

A number of embodiments have been described. Nevertheless, it will be understood that various modifications may be made without departing from the spirit and scope of the disclosure. Accordingly, other embodiments are within the scope of the following claims.

What is claimed is:

1. An apparatus for testing mechanical properties of a sample cement composition, comprising:
    an annular test chamber;
    a variable stress system in communication with the annular test chamber, the variable stress system operable to control pressure applied to a sample cement composition in the annular test chamber during and after curing of the sample cement composition; and
    one or more sensors coupled to the annular test chamber, the sensors operable to sense at least one of stress, strain and displacement from the sample cement composition in response to one or more changes applied to the annular test chamber by the variable stress system for determination of at least one mechanical property of the sample cement composition.

2. The apparatus of claim 1, the annular test chamber operable to cure the sample cement at curing conditions of a well bore.

3. The apparatus of claim 1, wherein the variable stress system comprises a variable pressure system and a variable temperature system, the variable pressure system and the variable temperature system operable to control a temperature and a pressure applied to the sample cement composition in the annular test chamber during curing of the sample cement composition and to vary a pressure applied to the sample cement composition in the annular test chamber after curing of the sample cement composition.

4. The apparatus of claim 1, further comprising:
   an outer pipe forming an outer wall of the annular test chamber;
   an inner pipe forming an inner wall of the annular test chamber; and
   wherein the variable stress system is operable to apply pressure changes to the sample cement composition through the inner pipe.

5. The apparatus of claim 1, further comprising a plurality of sensors coupled to the annular test chamber, the sensors comprising at least one of strain and displacement gauges mounted to the annular test chamber.

6. The apparatus of claim 1, wherein the sample cement composition is cured and tested without exposure to atmospheric conditions between curing and testing.

7. The apparatus of claim 1, wherein the mechanical property comprises at least one of Young's modulus or Poisson's ratio.

8. The apparatus of claim 1, wherein the variable stress system comprises a variable pressure system, the variable pressure system operable to vary a pressure applied to the sample cement composition in the annular test chamber.

9. The apparatus of claim 8, the variable pressure system operable to apply step pressure changes to the sample cement composition in the annular test chamber.

10. The apparatus of claim 8, wherein the variable stress system comprises a variable temperature system, the variable temperature system operable to vary a temperature applied to the sample cement composition in the annular test chamber.

11. The apparatus of claim 1, further comprising a plurality of sensors coupled to the annular test chamber, the sensors comprising stress sensors mounted in the annular test chamber.

12. The apparatus of claim 11, the stress sensors comprising a first stress sensor mounted on an outer diameter of the inner pipe and a second stress sensor mounted on an inner diameter of the outer pipe.

13. A method for determining mechanical properties for a sample cement composition, comprising:
   curing a sample cement composition at well bore pressure conditions in an annular test cell; and
   determining one or more mechanical properties of the sample cement composition based on at least one of stress, strain and displacement measurements from the sample cement composition in response to one or more pressure changes applied to the sample cement composition in the annular test cell.

14. The method of claim 13, wherein the mechanical properties comprise Young's modulus.

15. The method of claim 13, further comprising curing the sample cement composition at well bore temperature conditions.

16. The method of claim 13, wherein the mechanical properties comprise a plurality of Young's modulus, Poisson's ratio and tensile strength.

17. The method of claim 13, further comprising determining the one or more mechanical properties without exposing the sample cement composition to atmospheric conditions between curing and testing.

18. The method of claim 17, wherein the mechanical properties comprise Poisson's ratio.

19. A method for testing mechanical properties of cement for a well bore, comprising:
   sealing a sample cement composition in an annular test cell;
   applying a curing pressure and temperature to the sample cement composition in the annular test cell;
   measuring volume change to the sample cement composition in the annular test cell during curing;
   measuring at least one of stress, strain and displacement from the sample cement composition in the annular test cell during curing;
   changing pressure applied to the sample cement composition in the annular test cell in one or more steps; and
   measuring changes in at least one of stress, strain and displacement from the sample cement composition in the annular test cell caused by the pressure changes.

20. The method of claim 19, further comprising determining Young's modulus and Poisson's ratio of the sample cement composition based on the measurements.

* * * * *